(12) United States Patent
Dyba (10) Patent No.: US 7,999,935 B2
(45) Date of Patent: Aug. 16, 2011

(54) LASER MICROSCOPE WITH A PHYSICALLY SEPARATING BEAM SPLITTER

(75) Inventor: Marcus Dyba, Heidelberg (DE)

(73) Assignee: Leica Microsystems CMS GmbH, Wetzlar (DE)

(*) Notice: Subject to any disclaimer, the term of this patent is extended or adjusted under 35 U.S.C. 154(b) by 33 days.

(21) Appl. No.: 12/516,779

(22) PCT Filed: Aug. 31, 2007

(86) PCT No.: PCT/EP2007/059106
§ 371 (c)(1),
(2), (4) Date: May 28, 2009

(87) PCT Pub. No.: WO2008/064932
PCT Pub. Date: Jun. 5, 2008

(65) Prior Publication Data
US 2009/0323058 A1    Dec. 31, 2009

(30) Foreign Application Priority Data
Nov. 28, 2006  (DE) .................. 10 2006 056 429

(51) Int. Cl.
*G01J 3/44* (2006.01)
(52) U.S. Cl. ........................................... 356/301
(58) Field of Classification Search .................. 356/301, 356/72–73
See application file for complete search history.

(56) References Cited

U.S. PATENT DOCUMENTS

| 4,744,663 A | 5/1988 | Hamashima et al. |
| 2003/0160955 A1 | 8/2003 | Xie et al. |
| 2006/0238745 A1* | 10/2006 | Hashimoto et al. ............. 356/73 |

FOREIGN PATENT DOCUMENTS

| DE | 199 06 757 | 12/1999 |
| DE | 198 42 153 | 3/2000 |
| DE | 10257237 | 6/2003 |
| DE | 10 2004 034 971 | 2/2006 |
| EP | 1 211 544 | 6/2002 |

(Continued)

OTHER PUBLICATIONS

Liedtke, S. and Popp, J.: "Laser, Licht und Leben", Wiley-VCH Veriag GmbH & Co. KGaA, Weinheim, 2006, pp. 111-133.

(Continued)

*Primary Examiner* — Tarifur Chowdhury
*Assistant Examiner* — Abdullahi Nur
(74) *Attorney, Agent, or Firm* — Schlee IP International, P.C.; Alexander R. Schlee (57) ABSTRACT

The invention proposes a method for imaging at least one microscopic property of a sample and an apparatus with which the proposed method can be carried out. In the method, at least one coherent illumination light with at least one illumination wavelength is produced by means of at least one light source. The illumination light is imaged onto at least one region on or within the sample. Detection light emitted by the sample is split at least partially into incoherent detection light and into coherent detection light by means of at least on physically separating beam splitter. The coherent detection light is at least partially separated from the coherent illumination light by at least one beam-splitter element. The coherent detection light is detected. The proposed method can be used in particular for investigating the sample by means of coherent anti-Stokes-Raman scattering.

38 Claims, 2 Drawing Sheets

FOREIGN PATENT DOCUMENTS

EP          1 617 205        1/2006

OTHER PUBLICATIONS

Greve, M.: "High-Contrast Chemical Imaging with Gated Heterodyne Coherent Anti-Stokes Raman Scattering Microscopy", Appl. Physics B 81, 875 (2005).

Notification of Transmittal of Translation of the International Preliminary Report on Patentability, Form PCT/IB/338 for PCT/EP2007/059106.

International Preliminary Report on Patentability, Form PCT/IB/373 for PCT/EP2007/059106.

Written Opinion of the International Searching Authority, PCT/ISA/237 for PCT/EP2007/059106.

\* cited by examiner

LASER MICROSCOPE WITH A PHYSICALLY SEPARATING BEAM SPLITTER

CROSS-REFERENCE TO RELATED APPLICATIONS

This application is a national phase entry based on the International Patent Application PCT/EP2007/059106 filed on Aug. 31, 2007 that claims the priority of the German patent application DE 102006056429.4 dated Nov. 28, 2006. The entire content of this prior German patent application is herewith incorporated by reference.

BACKGROUND OF THE INVENTION

The invention relates to a device for imaging at least one microscopic property of a sample. Such devices are in particular used in the field of microscopy, in particular for analyzing biological or medical samples. Also other fields of use are possible. Further, the invention relates to the use of the device for a coherent laser spectroscopy method as well as to a method for imaging at least one microscopic property of a sample.

Particularly in the field of biology and medicine highly improved optical imaging techniques have been developed. In addition to the classical light microscopy that relies for the imaging on dispersion, reflection or absorption properties of a sample, increasingly methods are used where the molecular or atomic properties of the sample to be examined are used, or wherein the sample is modified in a predetermined manner (for example by dying or using marker molecules or marker groups), for improving by means of these modifications, the resolution and contrast of the image. Such methods are often referred to as "biophotonics". An overview over such methods can for instance be gathered from S. Liedtke and J. Popp: "Laser, Licht and Leben", Wiley-VCH Verlag GmbH & Co.KG aA, Weinheim, 2006, pages 111-133.

For the purpose of imaging, frequently the technology of fluorescence microscopy is used. For this purpose, a sample is illuminated by illumination light of one or more wavelengths and the light emitted by the sample as a reaction of this illumination light is a luminescent light of shifted frequency (i.e. of the fluorescence light and/or phosphorescence light) that is detected. For enhancing the spectral properties of the sample, frequently dying technology is used. For being able to also excite multiphoton transitions, frequently in addition to conventional light sources also lasers are used for exciting.

One difficulty mainly occurring in the course of fluorescence microscopy is to separate for the analysis the emitted luminescent light and the illumination and detection light from each other. For conventional fluorescence microscopes dichroic filters or mirrors are typically used that separate the illumination light from the luminescent light to be detected. Due to the Stokes shift, the luminescent light comprises typically a longer wavelength compared to the illumination light.

Such technology is, however, subject to various technical challenges. Such optical component parts with very specific spectral transparency or reflectivity properties are technically difficult to manufacture. Further, such component parts are typically non-flexible with regard to the transmitted or reflected wavelength so that a change of the illumination- and/or luminescence wavelength often requires a complete replacement of these selective optical elements. Another difficulty is that in many cases the illumination- and/or the luminescence-wavelength have a limited spectral width so that the illumination and luminescence light overlap spectrally. A separation of the illumination light and luminescence light only based on the wavelength is therefore very difficult.

From DE 198 42 153 C2 and DE 102 57 237 A1 technology is known making use of spatial separations of the illumination and luminescent light instead of a spectral separation. For the purpose of separation, the DE 198 42 153 C2 therefore suggest a partial transparent mirror that deflects light from the illumination light source to the object, but allows fluorescence light coming from the object to pass partially to the detector. For this purpose, the surface of the mirror comprises a reflecting mirror surface and a transparent mirror surface. The fluorescent light detected in the reverse direction illuminates the entire pupil plane and is therefore substantially in its entirety passing through the transparent areas of the spatial beam splitter.

Similarly, DE 102 57 237 A1 suggests means for a spatial separation of the illumination light from the detection light. Again, the arrangement shown comprises at least one reflecting first area and at least a transparent second area. The spatially splitting beam splitter is in this case positioned preferably in or close to the pupil plane. The fluorescent light detected in the reverse direction does also in this case illuminate the entire pupil plane and is therefore almost entirely passing the transparent areas of the spatially splitting beam splitter.

One advantage in using these spatially splitting beam splitters is that it is possible to abstain from using the spectral beam splitters that are disadvantageous and described above, as for example dichroic mirrors and beam splitters in combination with filter elements.

A disadvantage of the known fluorescence microscopes is that regardless of the described enhancements by using spatially splitting beam splitters the contrast has its limits, in particular in case of non-dyed or non-modified biological samples, as for instance in the case of CARS-microscopy. This results in particular from the detection irradiation that is in this case a coherent detection irradiation (also an irradiation of synchronously oscillating wave trains), is superseded by a background irradiation resulting in the background noise. Therefore, the signal-to-noise-ratio determines the contrast that can be achieved for the image in the case of the described fluorescence microscopy methods.

In addition to the described fluorescence methods a number of additional spectroscopic methods exist that can also be applied successfully in the field of biophotonics or microscopy. Among these methods in particular methods are mentioned that are based on the known principles of laser spectroscopy. One example for such methods is the so-called CARS-spectroscopy (coherent anti-Stokes Raman scattering) that is for example described as well in the above-mentioned publication by S. Liedtke and J. Popp. This spectroscopy is based on the simultaneous irradiation by photons of different excitation frequencies onto the sample wherein the difference in these excitation frequencies equals just to a frequency of a Raman-active oscillation transition in the sample. In this case the sample emits light of a frequency that equals the sum of an excitation frequency and the frequency of the Raman-active oscillation transition.

Also in case of CARS the problem occurs that the detection light comprises several portions of which one or more frequencies have to be detected separately and selectively. In particular the CARS-portion of the illumination light has to be detected separately from the Raman-irradiation. For the purpose of this separation several measuring schemes have been suggested, wherein the coherent properties of the detection light is used. One example for such a detection scheme is the so-called "gated heterodyne CARS"-method (GH- CARS), for example described in "High-contrast chemical imaging with gated heterodyne coherent anti-Stokes Raman scattering microscopy", Appl. Physics B 81, 875 (2005).

These known methods for separating the coherent illumination light from the background irradiation are, however, technically very sophisticated, since, as for example in case of GH-CARS, time resolution electronics with complex measuring schemes has to be used. The complexity lowers the attractivity of such methods for use in low cost microscopy methods. Moreover, these methods are prone to failures.

SUMMARY OF THE INVENTION

It is therefore an object of the invention to provide a device for imaging the properties of a sample that are particularly suitable in the field of biophotonics and avoid the disadvantages that have been described above in connection with prior art devices. In particular, it should be possible to manufacture the device at low cost and in a simple manner while at the same time images of a high contrast and a good signal-to-noise-ratio can be provided.

This object is achieved by a device with the features according to claim 1, a method with the features according to claim 19 and a use according to the features in claim 25. Advantageous further embodiments of the invention are described in the dependent claims, both individually or in combination thereof.

The invention is based, starting from the above-described prior art in the field of fluorescence microscopy, substantially on the idea of using spatially separating beam splitters, as for instance described in DE 198 42 153 C2 or DE 102 57 237 A1, i.e. the separation of the illumination light from the detection light is not carried out depending on the wavelength or spectrally by using the Stokes shift, but is accomplished by separating the beam splitter into a reflecting and a transparent area. In contrast to the methods described in these publications, however, not or not exclusively the fluorescence light is used for generating a signal, but the coherent light emitted by the sample. A significant idea of the invention is based on the idea to use a spatially separating beam splitter for separating coherent detection light from incoherent detection light. As such, the invention combines the idea known from fluorescence microscopy to use a spatially splitting beam splitter for separating the illumination light from the detection light and combine this idea with the advantages that can be derived from a coherent spectroscopy, and therefore also solves the problem of separating the incoherent background signal from the coherent detection signal, as for examples in the case of CARS-microscopy.

The suggested device comprises at least one light source for generating at least one coherent illumination light with at least one illumination wavelength or illumination frequency. Preferably, the light source comprises at least one laser, wherein the laser can be used in a pulsed operational mode (for example in the pico seconds or femto seconds range) as well as in the continuously operating mode. For achieving a high short-term intensity in particular short-pulsed lasers have proven to be suitable, for example pico or femto second lasers. Preferably, the light source comprises a light source providing variable wavelengths, in particular an adjustable wavelength, for example a dye laser, an adjustable gas laser, a diode laser or an adjustable solid state laser. For particular types of coherent spectroscopy where two or more wavelengths have to be provided, the device may comprise two or more separate or coupled laser sources, possibly also in combination with conventional light sources. Moreover, a single laser beam can for instance be split into two partial beams, wherein the frequency of at least one of the partial beams is shifted by a suitable optical element, for example an optical parametric oscillator. Subsequently, the at least two partial beams can be combined again, so that coherent illumination light comprising several illumination frequencies can be transmitted onto the sample.

In addition to the light source the device comprises imaging optics for imaging the at least one illumination light beam bundle onto at least a part within the sample. By imaging in particular a focusing can be understood, wherein the focusing is performed in at least one direction in space. In this manner, it is for instance possible to perform line scans (also see below). For example, such imaging optics can have one or more lenses, preferably one or more microscope objectives, as well as further optical elements, as for instance diaphragms, prisms or the like. Preferably, the imaging optics comprise confocal optics, as it is known to the skilled person for instance in the field of confocal microscopes. For this technology at least one confocal diaphragm is arranged in the detection beam path so that only one signal of a small volume segment within the sample is detected. In addition, a respective diaphragm can be provided in the illumination beam path.

Preferably, imaging optics and/or the device are designed such that a scanning device is provided and arranged such that the sample is scanned pointwise or linewise with the illumination light. Such scanning devices that are also known in the field of microscopy are based on a step-by-step moving of the sample in relation to the beam path of the illumination light bundle, or in the alternative or in addition, preferably by scanning the samples by means of a fast moving mirror, for example in a linewise or pointwise scanning manner. In this manner several areas of the sample (for example points or lines) can be illuminated stepwise.

The illumination light is preferably chosen such that it interacts with the sample. This interaction should be accomplished such that the sample emits as a response coherent detection light. Such interactions and processes are known in the field of laser spectroscopy, so that the illumination light and its properties can be chosen in accordance with the sample and/or modifications of the sample (for instance dying). For example, a multiphoton absorption process, the mentioned CARS, SHG (Second Harmonic Generation), frequency mixing or four-wave mixing, or simple reflection can be used as coherent laser spectroscopy methods. For optimizing the illumination light and its interaction with the sample it is also possible to perform first a spectroscopic wavelength scan of the sample.

Therefore, the detection light emanates from the sample and comprises the following parts: a first portion of the detection light is an incoherent portion. It comprises for example a luminescent portion (for example fluorescence or phosphorescence) that is typically incoherent and typically offset by the Stokes shift relative to the illumination light, or comprise depending on the circumstances further portions, as for instance (incoherent) Raman-light. Further, the detection light also comprises a coherent part that in itself is composed of several component parts. A first coherent part is such reflected detection light part as reflected by the sample, a carrier of holding the sample or a bracket holding the sample (or in a transparent arrangement, for instance F-CARS, transmitted detection light portion), that comprises typically a wavelength that is identical with the illumination of light. The second coherent detection light portion is a portion having a wavelength differing from the illumination light. For example, this may be the portion of frequency doubling in the sample, or the above described CARS-detection light. For unifying the terminology, all of these types of detection light are in the following referred to as "emitted from the sample", wherein the expression of emission in this case should comprise the detection light that is reflected or transmitted.

In contrast to the incoherent emitted scattered light that does not stand in any phase correlation to the illumination light this coherent detection light comprises a defined phase correlation to the illumination light. This coherent detection light can now be detected in a forward-operating arrangement (that means the detector and the illumination light source are provided on the opposite side of the sample) or in a reverse-operating arrangement (that means the illumination light source and the detector are provided on the same side of the sample).

The suggested device solves the problem of separating the various portions of the detection light by means of the first measure of providing at least one spatially splitting beam splitter in the beam path. This beam splitter can for instance be designed such as described in the above described publications DE 198 42 153 C2 or DE 102 57 237 A1. Accordingly, the spatially separating beam splitter can for instance comprise at least two areas of different transmission rate properties, wherein at least one first area comprises a high transmitivity and the second area comprises a high reflectivity. It is preferable (for avoiding heating-up of the spatially splitting beam splitter) to provide the second area with high reflectivity. For example, partially mirroring areas can be provided on a substrate that is transparent for the particular wavelengths.

The spatially splitting beam splitter is preferably arranged in the pupil plane, also in an imaging plane of the illumination light (and therefore based on the reversibility of the beam path, also of the coherent detection light). For example, it can be a plane where the illumination light is focused. In the alternative, also a plane can be chosen in which the illumination light and the coherent detection light comprise a substantially smaller beam diameter (for example less than 20%, preferably less than 10%) as the incoherent detection light. Preferably, the incoherent detection light illuminates at the position of the spatially splitting beam splitter the opening through which it penetrates substantially in its entirety.

The function of the spatially splitting beam splitter is based on the fact that coherent detection light portions are imaged again into defined areas of the spatially splitting beam splitter, while incoherent light portions are preferably illuminating substantially the entire pupil. The reason for this is that a coherent signal from the sample space in the pupil plane of the spatially splitting beam splitter interferes such that the same structure is generated there as the previously transmitted illumination signal. An incoherent signal is composed of a plurality of independent point illuminators, wherein each individual one illuminates the entire pupil plane of the spatially splitting beam splitter. The sum of all point illuminators does therefore also eliminate the entire pupil plane.

This effect is, as described above, used for a separation of the detection light emitted by the sample into a coherent portion and an incoherent portion. The separation takes place with high efficiency, a high suppressing ratio and can be implemented at low costs. Complex elements of selecting particular wavelengths can be omitted.

After separation of the coherent and incoherent light portions of the light emitted by the sample the coherent detection light portions, as described above, now consists only of portions of a wavelength of the illumination light and portions comprising a different wavelength as the wavelength of the illumination light. For separating of these portions, starting from the spatially splitting beam splitter, preferably provided downstream in the beam path, an additional beam splitter element is provided. This additional beam splitter element is adapted to separate the coherent detection light of the detection light wavelength from the coherent detection light with at least one wavelength differing from the detection light wavelength (the actual signal). The latter light portion is detected by at least one detection device.

The incoherent detection light can be detected by means of a detection device and can be used later for further analysis. In this manner, it is for instance possible to detect additional incoherent Raman-portions or luminescence portions and possibly generate multi-channel images. The incoherent detection signal can for instance be a Raman-, fluorescence-, phosphorescence-, or FRET (fluorescence resonant energy transfer)-signal. Further, it is possible to use the incoherent portions for an additional cleanup of the coherent signals (for example by subtracting the background noise). All image portions or also individual images can for instance be stored, for example as a function of at least one coordinate in space, or can also be displayed on a display screen.

For the detection device or an additional detection device it is generally possible to use common types of detection devices, as these are known to the person skilled in the art. In particular, in the detection of the coherent CARS-light or CARS-signal (also known for other types of laser spectroscopy), due to the often very weak signals, in particular avalanche photodiodes (in particular in the linewise arrangement for use in the line scanning method), photo multipliers (in particular multi-channel photomultipliers) or CCD-cameras (in particular again operating in a line-wise fashion), in particular so-called EMCCD-cameras (electron multiplier CCD camera) have proven to be preferable.

For the at least one additional beam splitter element for splitting the coherent detection light portions the skilled person may use known wavelength selective technology. For example, dichroic beam splitters, color filters or the like can be used. Also, polarization beam splitters can be used, wherein it is taken advantage that the coherent detection light can be modified to a different polarization state as the polarization state of the light comprising the illumination wavelength. For example, the illumination light can be polarized in a linear fashion, by means of a phase plate modified to a circular polarization, wherein the reflection at the sample results in a circular polarization of the opposite rotational direction, resulting by a second passing through the phase plate in a linear polarization of vertical polarization direction in comparison to the initial polarization of the illumination light. The detection light comprising a wavelength that differs from the illumination light and has passed the phase plate only once comprises therefore a different polarization so that a separation for example by means of a polarization beam splitter into coherent detection light of the illumination light wavelength and coherent detection light of a wavelength differing from the illumination light wavelength can be accomplished. Also other types of separation of this detection light portion are possible, as well as combinations of the above described separation methods. Generally, the additional beam splitter element may also comprise an additional spatially splitting beam splitter.

The above described device and the described method can in particular be used such that the coherent illumination light bundle may comprise at least one exciting frequency of an oscillation transition in the sample and whole-number multitudes of the frequency of the illumination light may correlate to the exciting frequency of an oscillation transition in the sample. In the alternative or in addition the sample can be irradiated by at least two exciting frequencies wherein the at least two exciting frequencies are chosen such that a linear combination of these exciting frequencies (for example $a1\omega1+a2\omega2$ with $a1$, $a2$ integers, positive or negative) equals to the frequency of a quantum mechanical transition in the sample. An example for such a method is described in CARS-spectroscopy or CARS-microscopy. The device according to the invention may use in addition to the CARS also additional coherent laser spectroscopy methods, for example multiphoton absorption spectroscopy or exciting/detection spectroscopy with time-delayed pulses.

BRIEF DESCRIPTION OF THE DRAWINGS

Embodiments of the present invention are shown in the drawings and are described in more detail in the following.

In the drawings show.

DETAILED DESCRIPTION OF THE DRAWINGS

Figure 1:
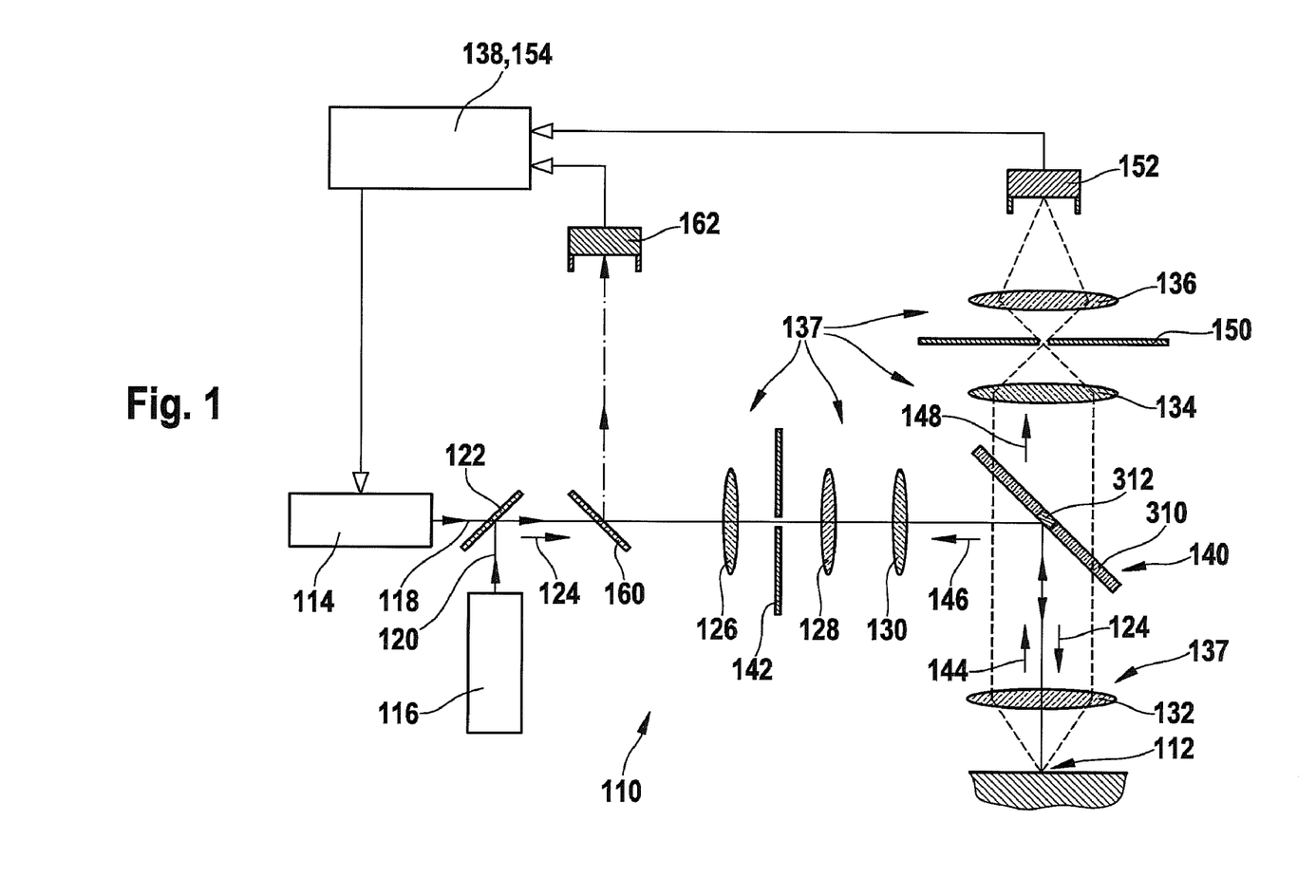
FIG. 1 an embodiment of the device for imaging at least one microscopic property of a sample object, comprising a beam splitter splitting beams in a spatial manner and an additional beam splitter element.

FIG. 1 shows a device 110 according to the invention for imaging at least one microscopic property of a sample 112. The individual elements of the device 110 are shown in a highly schematic manner and are only provided for discussing the functional principles. It is further assumed that the sample 112 is preferably a biological sample provided on a respective sample carrier plate and the spatial structure of the sample should be imaged.

Figure 2:
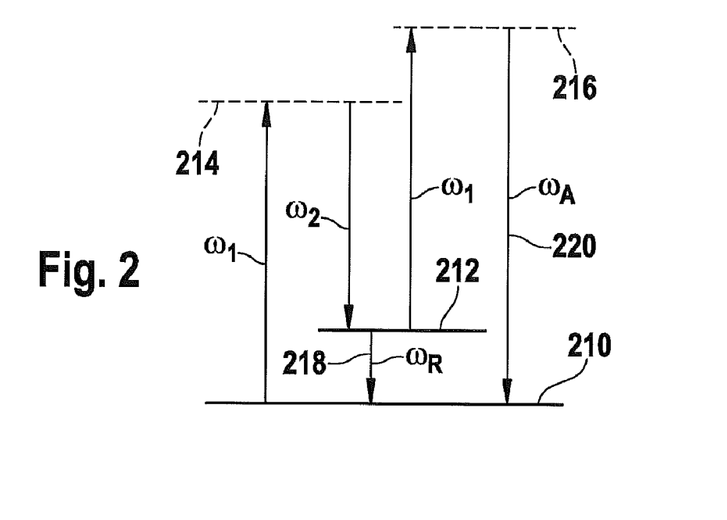
FIG. 2 a schematic CARS term diagram.

For imaging of the spatial structure of the sample the measuring principle of coherent anti-Stokes Raman spectroscopy (CARS) is used. FIG. 2 shows a schematic term diagram demonstrating this type of coherent laser spectroscopy that will be discussed in connection with FIG. 1. However, it should be pointed out that the device 110 as shown in FIG. 1 can also be used for other types of coherent laser spectroscopy.

The device 110 according to FIG. 1 comprises in addition two coherent light sources 114, 116 that are in this specific embodiment shown as laser light sources. For this purpose, the first laser 114 is designed such that it emits an illumination light portion 118 comprising an illumination frequency $\omega1$ (in FIG. 1 denoted by the reference numeral 118), while the second laser emits an illumination light portion 120 comprising a frequency $\omega2$, and is denoted in FIG. 1 symbolically with reference numeral 120. Both illumination light portions 118, 120 are combined by a beam splitter 122 and provide the illumination light 124. The beam splitters 122 and 160 can also be combined into one and be designed as acousto optical beam splitters, for instance designed as an AOBS (Acousto Optical Beam Splitter), as for instance described in DE 199 06 757 B4.

As can be gathered from the term diagram according to FIG. 2, the illumination light portions 118, 120 have been chosen to have such frequencies that the differences between the frequencies are just in the range of Raman active oscillation transition in the sample 112. For this purpose, it is for example possible (for example by means of the previous spectroscopic testing) to make use of the properties of the sample itself, or it is possible, as described above, to stain the sample, for example by means of a dye and/or a chemical modification that provides such a Raman active transition. In FIG. 2 the base state is denoted with reference numeral 210 and the Raman-active state is denoted with reference numeral 212. The states 214 and 216 are virtual states. As it can be gathered from FIG. 2, the sample 112 emits during the transition from the Raman-active state 212 to the base state 210 a Raman-signal 218 of the frequency $\omega R$ that is incoherent, as well as starting from the virtual state 216 a light of the frequency $\omega A=2\omega1-\omega2$. This light is referred to in the following as the CARS-signal 220. The CARS-signal 220 is, in contrast to the Raman-signal 218, a coherent emitted irradiation.

The device 110 comprises a plurality of lenses 126-136 provided in the beam path, jointly forming imaging optics 137. The lenses 126 to 136 are shown in FIG. 1 only schematically, wherein the image forming can also be designed differently as shown in FIG. 1. Moreover, also the beam paths of the respective light beams are only shown schematically.

By means of the lenses 126-132 the illumination light 124 is projected onto the sample 112. For this purpose, for instance one or more lenses 126-132 can be formed as cylindrical lenses or similar optical elements that are suited for providing a line-shaped focusing of the illumination light 124 onto the sample 112. Further, as not shown in FIG. 1, a scanning device can be provided, for example in the form of one or more movable mirror elements that are provided such that the position of the illumination light on the sample 112 can be changed, so that the sample 112 can be scanned, for example controlled by means of a control device 138.

Figure 3A:
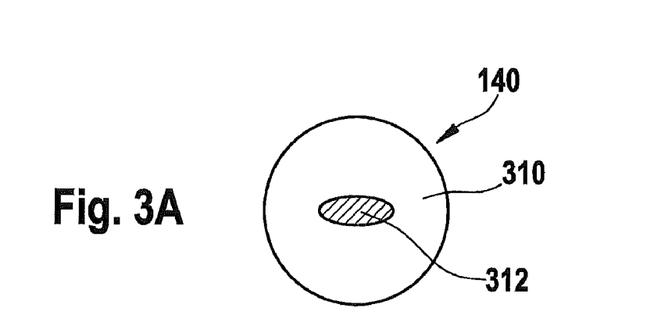
FIGS. 3A and 3B examples for spatially splitting beam splitters for the use in a device according to FIG. 1.
Figure 3B:
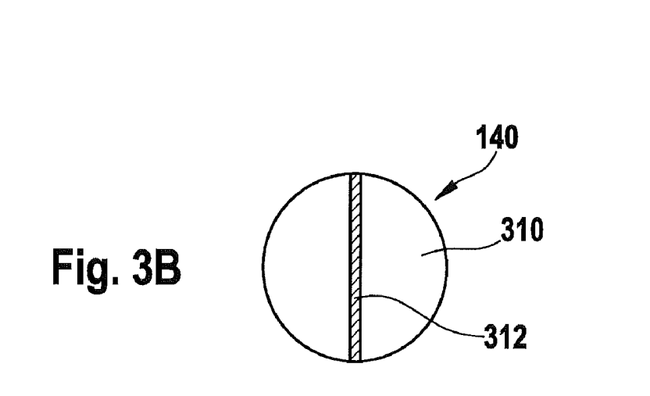

A spatially splitting beam splitter 140 is provided in the beam path of the illumination light 124. With regard to the specific embodiment of this spatially splitting beam splitter 140 it is for instance referred to the description above and the prior art cited therein. Preferred embodiments of such spatially splitting beam splitters 140 are shown in FIGS. 3A and 3B. Accordingly, the spatially splitting beam splitters shown in these embodiments comprise a first area 310 and a second area of 312. The first area 310, in this case covering the majority of the spatially splitting beams splitter 140, comprises (for example substantially wavelength-indifferent) a high transmission rate (for example a transmission rate of more than 90%, or, preferably, more than 95% for all frequencies shown in FIG. 2), while the second area 312 comprises a high reflectivity (for example a reflectivity exceeding 90%, or preferably, exceeding 95%). This second area 312 (in FIGS. 3A and 3B demonstrated by hatched lines), however, comprises a high reflectivity for the illumination frequencies $\omega1$ and $\omega2$ as well as for the CARS-signal 220 of the frequency $\omega A$. For example, the second area 312 can be created by partial evaporation deposition onto a transparent substrate of the spatially splitting beam splitter 140, for example by a evaporation deposition of metallic and/or dielectric layers, for example by using stencils. Also different manufacturing techniques can be used. In the alternative, the spatially splitting beam splitter can be provided as a MEMS-Array (MEMS=Micro Electro Mechanical System). It is particularly preferable if, as shown in FIG. 3A, the second area 312 is substantially round or (for an arrangement at preferably 45 degrees) oval.

In analogy, in FIG. 3B a stripe-shaped second area 312 is shown, wherein preferably also in this case the second area 312 comprises a width of 0.5 mm or less. Also in this case, the ratio of the areas is in the range of percentage. The arrangement shown in FIG. 3B is particularly suited for scanning in lines. It should be noted that in addition to the embodiments of the spatially splitting beam splitter 140 shown in FIGS. 3A and 3B also other embodiments are possible, for example embodiments where the transmission and reflection properties are inverted in comparison to the properties shown in FIGS. 3A and 3B (that means for example comprise a central area 312 of high transmission and a peripheral area 312 of high reflectivity). Also arrangements where more than one area 310, 312 is used are possible, for example embodiments having several line-shaped areas 312 in analogy to the embodiment shown in FIG. 3B, for example several lines arranged in parallel to each other or any other pattern.

The spatially splitting beam splitter 140 according to the device 110 shown in FIG. 1 can be used for several purposes. A first object achieved by this spatially splitting beam splitter 140 is to guide the illumination light 124 onto the sample 112. For this purpose, the imaging optics 137, in particular the lenses 126-130 and possibly a diaphragm 142 can be positioned such that the second area 312 that is highly reflective with respect to the illumination light 124 can be provided at or close to the focal point or the pupil of the illumination light 124, for example at an image of the diaphragm 142 through the lenses 128 and 130.

The second effect of the spatially splitting beam splitter 140 is, as described above, to separate the detection light 144 emitted by the sample 112 from the illumination light 124. This detection light, that is demonstrated in FIG. 1 symbolically by arrow 144, consists as described above of a coherent portion (arrow 146 in FIG. 1) and an incoherent portion 148. The coherent detection light portion 146 follows precisely the beam path of the coherent illumination light 124 based on the reversibility of the beam path and the coherent properties of the light. Accordingly, this detection light portion 146 is imaged onto the second area 312 of the spatially splitting beam splitter 140 and is reflected back in direction of the light sources 114, 116. In contrast, the incoherent detection light portion 148 that is emitted by the sample 112 into all directions in space and illuminates for instance the entire pupil opening of the lens 132 follows the beam path that is shown in FIG. 1 symbolically by the dotted line. Accordingly, this incoherent detection light portion 148 illuminates substantially the entire opening of the spatially splitting beam splitter 140, i.e. is transmitted substantially in its entirety by this spatially splitting beam splitter 140. The portion of the incoherent detection light that is reflected back by the second portion 312 of the spatially splitting beam splitter 140 in the direction of the light sources 114, 116 is, due to the preferably uniform illumination and the small ratio between the second area 312 and the first area 310 (see above), so insignificant that it can be disregarded. The incoherent detection light portion 148 is imaged by means of additional lenses 134, 136 as well as another diaphragm 150 onto an additional detection device 152 that transmits its signal to an electronic analyzing device 154.

These coherent detection light portions are separated by means of an additional beam splitter element 160, for example a dichroic mirror, or by a different additional beam splitter element according to the above description. The coherent detection light 146 is transmitted to a detection device 162, the output signals from which are transmitted to an electronic analyzing device 154. These signals correlate substantially with the CARS-signal 220 according to the term diagram shown in FIG. 2, also comprising light of the frequency ωA. The control device 138 of the electronic analyzing device 154 can for example be designed such that it controls a CARS-process for analyzing the sample 112 entirely or in part in an automated fashion. This allows, for example, to predetermine the wavelengths of the lasers 114, 116 in an automated fashion by means of a control device 138. Further, the control device 138 can communicate (with non-shown) scanning optics for generating based on suitable controls signals the related spatial imaging information and if desired to output this information to a user. The control device 138 and/or the electronic analyzing device 154 are accordingly in an advantageous manner programmed such that it can perform the above-described tasks. Also the above-described multichannel imaging or similar imaging processes that are based on the signals provided by the detection devices 152, 162 can be performed by the electronic analyzing device 154.

Finally, it is pointed out that the device 110 according to the embodiments shown in FIG. 1 is preferably designed as a confocal imaging device for providing an optimum resolution for the imaging of the imaging information relating to the sample 112. For this purpose, a spatial diaphragm 150 or a related imaging optics 134, 136 can be inserted in front of each detection device. The process according to the invention for analyzing the sample 112 by means of a CARS-process and by means of a spatially splitting beam splitter 140 can, however, also be achieved by a different arrangements, for example non-confocal arrangements of the device 110. Further, it is pointed out that the device shown in FIG. 1 is a device for the detection of CARS-signals 220 in a reverse mode, a method that is typically known as EPI-CARS. In the alternative or in addition it is possible to detect the CARS-signal 220 in the forward direction (in case of a partially transparent sample 112) which is also possible underneath the sample 112 shown in FIG. 1. Also in this case separation between coherent and incoherent detection light portions 146, 148 by means of a spatially splitting beam splitter 140 can be performed. The additional arrangements, in particular for separating the coherent detection light 146 (in particular the CARS-signal 220) and the coherent illumination light 124 are performed according to the arrangement shown in FIG. 1.

REFERENCE NUMERALS 110 imaging device for imaging at least one microscopic property of a sample
112 sample
114 laser 1
116 laser 2
118 illumination light portion ω1
120 illumination light portion ω2
122 beam splitter
124 illumination light
126-136 lenses
137 imaging optics
138 control device
140 spatially splitting beam splitter
142 diaphragm
144 detection light
146 coherent detection light
148 incoherent detection light
150 diaphragm
152 detection device
154 electronic analyzing device
160 additional beam splitter element
162 detection device
210 base state
212 Raman-active state
214 virtual state
216 virtual state
218 Raman-signal
220 CARS-signal
310 first area, high transmitivity
312 second area, high reflectivity

The invention claimed is:

1. Device for imaging at least one microscopic property of a sample, comprising: at least one light source for generating at least one coherent illumination light of at least one illumination light wavelength;
   at least one optics for illuminating at least one area within or on the sample with the at least one coherent illumination light;
   a spatially splitting beam splitter for separating at least in part the light from the sample into at least one coherent detection light emitted by the sample and at least one incoherent detection light emanating from the sample, wherein the spatially splitting beam splitter comprises at least a first area of high transparency of a first shape and a second area of high reflectivity of a second shape that differs from the first shape so that the spatially splitting beam splitter transmits or reflects light selectively depending on the areas of first and second shapes where light is incident on for splitting the incident light into the at least one coherent detection light emitted by the sample and the at least one incoherent detection light emanating from the sample;
   at least one additional beam splitter element provided in the beam path for separating the at least one coherent detection light from the at least one coherent illumination light; and
   at least one detection device for detection of the coherent detection light.

2. Device according to claim 1, further comprising an additional detection device for detecting the incoherent detection light emitted by the sample.

3. Device according to claim 2, wherein at least one of the at least one detection device for detection of the coherent detection light and additional detection device for detecting the incoherent detection light emitted by the sample comprises one of the following detection components:
   an avalanche photodiode,
   an APD-array;
   a photomultiplier,
   a multi-channel photomultiplier;
   a CCD camera,
   a CCD line camera;
   an EMCCD; and
   an EMDCCD line camera.

4. Device according to claim 1, wherein the coherent detection signal is one of the group consisting of CARS signal, SHG signal, four-wave mixing signal, and frequency mixing signal.

5. Device according to claim 1, wherein the incoherent detection signal is one of the group consisting of a Raman signal, fluorescence signal, phosphorescence signal, and FRET signal.

6. Device according to claim 1, wherein the beam splitter element that is arranged in addition in the beam path is designed such as to separate the reflected coherent detection light from the illumination light.

7. Device according to claim 1, wherein the beam splitter element that is arranged in addition in the beam path is designed such as to separate the reflected coherent detection light from the illumination light based on different polarization modes.

8. Device according to claim 1, wherein the beam splitter element that is arranged in addition in the beam path is designed such as to separate the reflected coherent detection light of different wavelength in comparison to the wavelength of the illumination light from that illumination light.

9. Device according to claim 1, wherein the at least one light source comprises at least one laser.

10. Device according to claim 1, wherein the imaging by means of the optics comprises focusing in at least one spatial direction.

11. Device according to claim 1, wherein the spatially splitting beam splitter comprises a partially mirroring, transparent substrate.

12. Device according to claim 1, wherein the at least one area of the first area and the second area comprises at least one of the following shapes from the group consisting of:
    at least a substantially circular shape, preferably provided on the optical axis of the spatially splitting beam splitter;
    at least an approximately oval or elliptical shape, preferably provided on the optical axis of the spatially splitting beam splitter;
    at least an approximate line shape, preferably extending through the optical axis of the spatially splitting beam splitter and perpendicular to the optical axis of the spatially splitting beam splitter;
    a line-shaped grating; and
    a point-shaped grating.

13. Device according to claim 1, characterized in that the spatially splitting beam splitter comprises a MEMS-array.

14. Device according to claim 1, wherein the light source comprises at least one light source of a variable wavelength.

15. Device according to claim 14, wherein the light source of a variable wavelength is one of the following group of lasers consisting of: a dye laser, a gas laser, a diode laser, and a solid state laser.

16. Device according to claim 1, wherein the light source comprises at least one pulsed light source.

17. Device according to claim 16, wherein the pulsed light source is at least one of a pico-second laser and a femto-second-laser.

18. Device according to claim 1, wherein the spatially splitting beam splitter is arranged in the pupil plane of the illumination light or in the vicinity of that pupil plane.

19. Device according to claim 1, wherein the additional beam splitter element comprises at least one of the following group of elements consisting of:
    a polarization beam splitter;
    a dichroic beam splitter;
    a color filter;
    an additional spatially splitting beam splitter;
    an acousto optical beam splitter; and
    an AOBS.

20. Device according to claim 1, further comprising at least one scanning device comprising one or more rotatable mirrors, wherein the scanning device is designed such as to scan the sample in at least one of pointwise and linewise manner with the illumination light.

21. Device according to claim 1, wherein the device comprises a laser scanning microscope with a confocal detection device.

22. Device according to claim 1, further comprising an electronic analyzing device for analyzing an intensity of the coherent detection light.

23. Device according to claim 22, wherein the analyzing device is designed such that it can perform at least one of the following steps:
    the intensity of the coherent detection light is adjusted according to the intensity of the incoherent detection light;
    at least one of the intensity of the coherent detection light and the intensity of the incoherent detection light is at least one of stored as a function of a spatial coordinate as imaging information and displayed on a display screen in the form of a multichannel image.

24. Device according to claim 1, wherein at least one light source is arranged to generate illumination light of at least two illumination light wavelengths.

25. Device according to claim 24, wherein the at least one light source comprises a device for splitting the illumination light into at least two partial beams, as well as at least one device for shifting of the frequency of at least one of the partial beams.

26. Use of a device according to claim 1 for at least one of the following coherent laser spectroscopy methods in the group consisting of: coherent anti-Stokes Raman spectroscopy (CARS), Multiphoton absorption spectroscopy; Excitation/Detection spectroscopy (pump-probe spectroscopy) with time-wise delayed pulses.

27. Method for imaging at least one microscopic property of a sample, the method comprising the following steps:
   a) generating a coherent illumination light of at least one illumination wavelength by means of at least one light source;
   b) imaging the illumination light on or into at least part of the sample;
   c) splitting the detection light that is emitted from the sample by means of a spatially splitting beam splitter into at least in part incoherent detection light and coherent detection light, the spatially splitting beam splitter comprising at least a first area of high transparency of a first shape and a second area of high reflectivity of a second shape that differs from the first shape so that the spatially splitting beam splitter transmits or reflects light selectively depending on the areas of first and second shapes where light is incident on for splitting the incident light into the at least one coherent detection light emitted by the sample and the at least one incoherent detection light emanating from the sample;
   d) separating the coherent detection light at least partially by means of an additional beam splitter element from the coherent illumination light; and
   e) detecting the coherent detection light.

28. Method according to claim 27, further comprising the step of detecting in addition the incoherent detection light.

29. Method according to claim 27, further comprising the steps of choosing at least one of the light source and the illumination light such that the sample is illuminated by at least two illumination frequencies; and
   choosing the at least two illumination frequencies such that a linear combination of these illumination frequencies equals the frequencies of the quantum mechanical transition in the sample.

30. Method according to claim 27, further comprising the method step of using a first illumination frequency and a second illumination frequency such that the difference between the two illumination frequencies equals to the Raman-active oscillation transition in the sample.

31. Method according to claim 27, further comprising the method step of generating the coherent detection signal by means of Raman, SHG, four-wave mixing, or frequency mixing.

32. Method according to claim 27, further comprising the method step of generating the incoherent detection signal by Raman, fluorescence, phosphorescence, or FRET.

33. Method according to claim 27, further comprising the method step of using an additional beam splitter element in method step d) for separating coherent detection light having a frequency that equals the sum from one of the illumination frequencies and the frequency of the Raman-active oscillation transition from the coherent detection light of the illumination frequency.

34. Method according to claim 27, further comprising the method step of using an additional beam splitter element in method step d) for separating the coherent detection light from the illumination light after it has been polarized into a different polarization state.

35. Method according to claim 27, further comprising the method step of using an additional beam splitter element in the method step d) for separating coherent detection light reflected by the sample and being of the same frequency as the illumination light from that illumination light.

36. Method according to claim 27, further comprising the method step of using an additional beam splitter element in the method step d) for separating coherent detection light reflected by the sample and being double the frequency of the illumination light from that illumination light.

37. Method according to claim 27, further comprising the method step of using an additional beam splitter element in the method step d) for separating coherent detection light from the illumination light by means of one of the group consisting of a polarization beam splitter, dichroic beam splitter, color filter, additional spatially splitting beam splitter and acousto optical beam splitter, and AOBS.

38. Method according to claim 27, further comprising the method step of using a detection device in method step e) for detecting coherent detection light of a frequency that equals the sum of one of the two illumination frequencies and the frequency of the Raman-active oscillation transition.

* * * * *